US010995357B2

(12) United States Patent
Ingber et al.

(10) Patent No.: US 10,995,357 B2
(45) Date of Patent: *May 4, 2021

(54) RAPID ANTIMICROBIAL SUSCEPTIBILITY TESTING BASED ON A UNIQUE SPECTRAL INTENSITY RATIO ANALYSIS VIA SINGLE FLUORESCENCE MEMBRANE DYE STAINING AND FLOW CYTOMETRY

(71) Applicant: POCARED Diagnostics LTD., Rehovot (IL)

(72) Inventors: Gal Ingber, Oranit (IL); Moshe Ben-David, Tel Aviv (IL); Mushki Fridman, Kiryat Malachi (IL); Yael Gluckman, Rehovot (IL); Dina Gohman, Holon (IL); Orly Hammer Munz, Ness Zionna (IL); Anita Shinderman, Ashdod (IL); Eran Zahavy, Rehovot (IL)

(73) Assignee: POCARED Diagnostics LTD.

(*) Notice: Subject to any disclaimer, the term of this patent is extended or adjusted under 35 U.S.C. 154(b) by 39 days.

This patent is subject to a terminal disclaimer.

(21) Appl. No.: 15/866,060

(22) Filed: Jan. 9, 2018

(65) Prior Publication Data

US 2018/0195964 A1 Jul. 12, 2018

Related U.S. Application Data

(60) Provisional application No. 62/443,850, filed on Jan. 9, 2017, provisional application No. 62/504,205, filed on May 10, 2017, provisional application No. 62/504,903, filed on May 11, 2017, provisional application No. 62/443,854, filed on Jan. 9, 2017, provisional application No. 62/504,152, filed on May 10, 2017, provisional application No. 62/504,851, filed on May 11, 2017.

(51) Int. Cl.

| | |
|---|---|
| *C12Q 1/18* | (2006.01) |
| *G01N 21/64* | (2006.01) |
| *G01N 1/30* | (2006.01) |
| *G01N 15/14* | (2006.01) |
| *G01N 15/10* | (2006.01) |

(52) U.S. Cl.
CPC .............. *C12Q 1/18* (2013.01); *G01N 1/30* (2013.01); *G01N 15/14* (2013.01); *G01N 21/6428* (2013.01); *G01N 21/6486* (2013.01); *G01N 15/1456* (2013.01); *G01N 21/6452* (2013.01); *G01N 2001/302* (2013.01); *G01N 2015/1006* (2013.01); *G01N 2015/1488* (2013.01); *G01N 2021/6417* (2013.01); *G01N 2800/52* (2013.01)

(58) Field of Classification Search
CPC .......... G01N 21/6486; G01N 21/6428; G01N 15/14; G01N 1/30; G01N 2015/1006; G01N 15/1456; G01N 2015/1488; G01N 2800/52; G01N 2021/6417; G01N 21/6452; G01N 2001/302; C12Q 1/18
See application file for complete search history.

(56) References Cited

U.S. PATENT DOCUMENTS

| | | | |
|---|---|---|---|
| 8,309,897 B2 | 11/2012 | Ingber | |
| 8,519,358 B2 | 8/2013 | Ingber et al. | |
| 8,804,114 B2 | 8/2014 | Ingber | |
| 8,808,649 B2 | 8/2014 | Ingber et al. | |
| 9,632,085 B2 | 4/2017 | Super et al. | |
| 2001/0039031 A1* | 11/2001 | Boeufgras | C12Q 1/04 435/32 |
| 2007/0166780 A1 | 7/2007 | Wilson | |
| 2008/0220465 A1 | 9/2008 | Ingber et al. | |
| 2011/0093207 A1 | 4/2011 | Ingber et al. | |
| 2011/0177549 A1* | 7/2011 | Glukhman | C12Q 1/06 435/39 |
| 2012/0196271 A1 | 8/2012 | Ingber | |
| 2014/0246389 A1 | 9/2014 | Ingber | |
| 2015/0064703 A1* | 3/2015 | Super | C12Q 1/18 435/6.12 |
| 2015/0152467 A1 | 6/2015 | Ingber et al. | |
| 2018/0010165 A1 | 1/2018 | Zahavy | |

FOREIGN PATENT DOCUMENTS

| | | |
|---|---|---|
| AU | 2013225823 A1 | 9/2014 |
| CA | 2973543 A1 | 7/2016 |
| WO | 2016142825 A1 | 9/2016 |

OTHER PUBLICATIONS

Zahavy, E et al. Abstract 426/B295: Live/dead bacteria discrimination by styryl fluorescence staining and spectral intensity ratio analysis. Cyto 2015, 30th Congress of the International Society of Advancement of Cytometry, Glasgow, UK. Jun. 26-30, 2015. Program Book. pages 249-250. (Year: 2015).*
Artemova, T et al. Isolated cell behavior drives the evolution of antibiotic resistance. Molecular Systems Biology. 2015. 11: 822. 11 pages. (Year: 2015).*
"Sepsis Fact Sheet", https://www.sepsis.org/faq/"Sepsis Fact Sheet", 2 pages.
"Sepsis (Blood Poisoning)", https://www.medicinenet.com/sepsis/article.htm, Apr. 24, 2018, 10 pages.
"Guidance for Industry and FDA, Class II Special Controls Guidance Document: Antimicrobial Susceptibility Test (AST) Systems", Aug. 28, 2009, FDA, 42 pages.

(Continued)

*Primary Examiner* — Renee Claytor
*Assistant Examiner* — Susan E. Fernandez
(74) *Attorney, Agent, or Firm* — The Webb Law Firm

(57) ABSTRACT

Single dye fluorescent staining and the combination of differences in both intensity and spectral emission permit determination of the minimum concentration of an antibiotic needed to inactivate bacteria (Minimum Inhibitory Concentration (MIC)), thereby providing a means for rapid Antibiotic Susceptibility Testing (AST). This allows for a quick and easy means for clinicians to determine a suitable treatment regimen for patients suffering from bacterial infections and those that eventually lead to sepsis.

22 Claims, 11 Drawing Sheets

(56) References Cited

OTHER PUBLICATIONS

Singh et al., "Rapid Test for Distinguishing Membrane-Active Antibacterial Agents", Journal of Microbiological Methods, 2006, pp. 125-130, vol. 67.
Zahavy et al., "Rapid Atibiotic Susceptibility Determination for Yersinia pestis Using Flow Cytometry Spectral Intensity Ration (SIR) Fluorescence Analysis", Journal of Fluorescence, 2018, pp. 1151-1161, vol. 28.

* cited by examiner

RAPID ANTIMICROBIAL SUSCEPTIBILITY TESTING BASED ON A UNIQUE SPECTRAL INTENSITY RATIO ANALYSIS VIA SINGLE FLUORESCENCE MEMBRANE DYE STAINING AND FLOW CYTOMETRY

CROSS REFERENCE TO RELATED APPLICATIONS

This application claims the benefit of U.S. Provisional Patent Application No. 62/443,850 entitled "Rapid Antimicrobial Susceptibility Testing Directly from Blood Culture Based on a Unique Spectral Intensity Ratio (SIR) Analysis by Flow Cytometry" filed Jan. 9, 2017, and U.S. Provisional Patent Application Nos. 62/504,205 and 62/504,903, both entitled "Rapid Gram Negative Antimicrobial Susceptibility Testing Directly From Positive Blood Culture Based on a Unique Spectral Intensity Ratio Analysis via Single Fluorescence Membrane Dye Staining and Flow Cytometry" and filed May 10, 2017 and May 11, 2017, respectively.

This application additionally claims the benefit of U.S. Provisional Patent Application No. 62/443,854 entitled "Rapid Antimicrobial Susceptibility Testing From Clinical Isolates Based on a Unique Spectral Intensity Ratio (SIR) Analysis by Flow Cytometry" filed Jan. 9, 2017, and U.S. Provisional Patent Application Nos. 62/504,152 and 62/504,851, both entitled "Fast Antibiotic Susceptibility Testing Utilizing a Unique Spectral Intensity Ratio Analysis via Single Fluorescence Membrane Dye Staining and Flow Cytometry" filed May 10, 2017 and May 11, 2017, respectively.

The above-referenced provisional applications are hereby incorporated by reference in their entirety.

BACKGROUND OF THE INVENTION

Field of the Invention

Intensity of bacterial infections can vary depending on the microbe causing the infection and the virulence of the microbe. As a result, identification of the microbe is essential for proper treatment. For instance, sepsis affects over 26 million people worldwide each year and is the largest killer of children—more than five million each year (see, for instance, https://www.sepsis.org/faq/"Sepsis Fact Sheet"). Mortality rates from sepsis in intensive-care units range from 40% to 60% worldwide, with one cause of death being that patients were initially treated with inappropriate antibiotic therapy (https://www.medicinenet.com/sepsis/article.htm). This is largely because it takes days to obtain a rigorous diagnosis of pathogen type, even in state-of-the art clinical microbiology laboratories. Moreover, patients who initially receive incorrect therapies exhibit a lower survival rate than those who are treated with optimal therapy from early in the course of the disease, have a shortened life expectancy, and are more likely to suffer from an impaired quality of life (https://www.sepsis.org/faq/"Sepsis Fact Sheet"). Thus, the speed of pathogen diagnosis in a patient with a microbial infection can significantly affect a patient's prognosis.

The current state of the art for detection of a microbial infection, which has essentially remained largely unchanged for the past 30 years, is to culture the blood in a hospital or commercial clinical microbiology laboratory. Liquid cultures can permit detection of the existence of some types of growing organisms in the fluid within 16 to 30 hours. This assay is not quantitative and without knowledge of the type of pathogen and their specific antibiotic sensitivities, only wide-spectrum antibiotics can be administered at this time, which are suboptimal at best. To identify the specific type of pathogen, and to carry out sensitivity testing to determine their responses to various potential antibiotic therapies, the pathogens growing in liquid medium must then be transferred to other growth media (e.g., agar plates). The total time for full diagnosis and sensitivity testing is commonly 3-7 days and empiric antibiotic treatment based on clinical symptoms is started well before the results of the antibiotic sensitivity are obtained.

Thus, rapid and reliable diagnostic and treatment methods are essential for effective patient care. Unfortunately, as indicated above, current antimicrobial susceptibility testing techniques generally require a prior isolation of the microorganism by culture (e.g., about 12 to about 48 hours), followed by a process that requires another about 6 to about 24 hours. For example, a confirmed diagnosis as to the type of infection traditionally requires microbiological analysis involving inoculation of blood cultures, incubation for 16-24 hours, plating the causative microorganism on solid media, another incubation period, and final identification 1-2 days later. Even with immediate and aggressive treatment, this can significantly affect a patient's prognosis, depending on the type of infection, and in some instances can lead to death.

Every hour lost before a correct treatment is administered can make a crucial difference in patient outcome. Consequently, it is important for physicians to determine rapidly the exact microbe causing the infection and what antibiotic(s) would be effective for the treatment. Given that current methods may take two days or more days to yield an answer, there is a strong need for a more rapid antibiotic sensitivity testing, preferably one that can identify specific antibiotic susceptibilities within only hours after blood samples are drawn. For instance, 1-3 hours, 1-5 hours, 1-10 hours, less than 24 hours, or after 24 hours, after blood samples are drawn. In another instance, 24 hours after blood samples are drawn and identified as being positive for a bacterial infection. A rapid test of this type would therefore permit physicians to initiate the optimal drug therapy from the start, rather than starting with a suboptimal or completely ineffective antibiotic, thereby greatly increasing clinical responsiveness.

Another issue encountered in treatment of patients with bacterial infections is a result of antibiotic resistance. Antimicrobial (i.e., antibacterial) resistance occurs when a microbe (i.e., bacteria and/or bacterial strain) acquires a genetic mutation, either spontaneously or by gene transfer, rendering it resistant to the treatment of one or more anti-bacterial agents, i.e., antibiotics. Drug-resistant organisms may acquire resistance to first-line antibiotics, necessitating the use of a second-line agent to which the microbe is sensitive. In the case of some bacterial strains that have gained resistance to multiple drugs, resistance to second- and even third-line antibiotics is sequentially acquired.

Resistance may take the form of a spontaneous or induced genetic mutation, or the acquisition of resistance genes from other bacterial species by horizontal gene transfer via conjugation, transduction, or transformation. Many antibiotic-resistance genes reside on transmissible plasmids facilitating their transfer. Antibiotic-resistance plasmids frequently contain genes conferring resistance to several different antibiotics.

The increasing rates of antibiotic-resistant bacterial infections seen in clinical practice stem from antibiotic use both within human and veterinary medicine. Any use of antibiotics can increase an evolutionary selective pressure in a population of bacteria, allowing resistant bacteria to thrive and non-resistant bacteria to die off. As resistance to antibiotics becomes more common, a greater need for alternative treatments arises. Antibiotic-resistance poses a grave and growing global problem to public health. With an increasing number of bacterial strains having resistance to antibiotics, individuals who require medicinal help are unable to acquire the proper treatment they require.

Therefore, in addition to determining the appropriate drug therapy, it is also crucial to determine the concentration/dosage of the drug therapy to be administered. Accordingly, it is an object of the present invention to provide: 1) quick, rapid determination of antibiotic susceptibility of a microbe, and 2) the minimum concentration needed for inhibition of the microbe(s).

Description of Related Art

Existing antimicrobial susceptibility testing (AST) techniques are lengthy processes. In general, current-day practice for identifying, isolating, and differentiating bacterial strains with and without antibiotic-resistance genes often involves a complex and lengthy process in microbiology labs. In the current processes, biological samples containing bacteria are first accepted into the lab. Systems like the BD Phoenix and bioMerieux Vitex 2 systems can be used to detect bacterial strains in manners known in the art. In another process, the biological samples are then streaked, using a sterilized loop, on agar plates containing a nutritionally-rich medium (for example, lysogeny broth or any other suitable broth). This agar plate contains spots that have been treated with an antibiotic. Once the specimen has been streaked on the plate, the agar plate is placed into a dedicated incubator for a minimum of 12 hours. The agar plates are then periodically checked for bacterial colony growth. As would be appreciated by one of ordinary skill in the art, if the biological sample contains bacteria, then bacterial colony growth is expected on the spots not containing the antibiotic. If the bacteria has not acquired an antibiotic-resistance gene, growth on the spots containing the antibiotic is not expected. However, if the bacterial strain has acquired an antibiotic-resistance gene, colony growth will occur on the spots that have been treated with the antibiotic. See for example, commonly owned U.S. Patent Application Publication No. 2008/0220465.

In another process, biological samples, upon collection, are sorted, labeled, and then inoculated into glass, round-bottom test tubes containing blood agar medium, or any other suitable nutritionally-rich growth medium (e.g., lysogeny broth), using a sterilized loop. The specimens are then inserted into a dedicated incubator for a 12 to 24-hour period. The samples are then observed and screened for positive (i.e., containing bacteria) and negative (i.e., not containing bacteria) cultures. Samples that appear to contain positive cultures are processed in order to isolate and suspend the bacteria in a biochemical fluid. This process involves suspension, dilution, vortexing, and turbidity measurements resulting in biochemical waste products. The cultures are then subjected to a species identification and antibiotics susceptibility tests, which exposes the bacterial suspensions to multiple reagents. After another 6 to 24-hour incubation period, the findings are interpreted and reported by lab technicians. This entire process generally takes at least 11, or more, steps and at least 50 hours to obtain specimen results and the process is labor intensive.

Other processes to differentiate and identify between bacterial species and/or strains involves various types of nucleic acid sequencing methods. Briefly, DNA sequencing is the process of determining the precise order of nucleotides within a DNA molecule. It includes any method or technology that is used to determine the order of the four bases—adenine, guanine, cytosine, and thymine—in a strand of DNA. In these methods, once a biological sample is obtained, the bacteria contained in the biological sample needs to first be amplified. In other words, the biological sample is first collected and is then used to inoculate a suitable bacterial growth medium (e.g., blood growth medium or lysogeny broth). The inoculated sample is then grown at appropriate conditions for 12-24 hours. Upon growth, bacterial cells are pelleted from the culture medium, lysed, and processed to extract the bacterial DNA. Bacterial DNA is then cleaned, purified, and placed in a DNA sequencer. The growth of the bacteria and isolation of the bacterial DNA not only requires reagents but also produces bio-waste material, and is additionally a timely process. Additionally, nucleic sequencing methods require the use of primer sequences. A primer is a strand of short nucleic acid sequences (generally about 10 base pairs) that serves as a starting point for DNA synthesis. It is required for DNA replication because the enzymes that catalyze this process, DNA polymerases, can only add new nucleotides to an existing strand of DNA. By requiring primer sequences, this method additionally requires some minimal knowledge of the type of bacterial strain. Sequencing, as indicated, can additionally be time consuming and expensive.

Once the microbe is identified, the patient is then treated with an antibiotic. In some cases, the initial concentration/dosage may not be effective, due to a variety of reasons, such as antibiotic resistance. As a result, by the time a patient receives the appropriate antibiotic, at the correct dosage, prognosis may be significantly hindered.

Therefore, in view of the foregoing, a rapid antimicrobial susceptibility testing method is required in order to quickly provide effective treatment to a patient in need thereof.

SUMMARY OF THE INVENTION

The present invention is a method for determining a minimum inhibitory concentration of one or more bacteria in a sample comprising the steps of:
  a. preparing a plurality of bacterial suspensions in a plurality of receptacles,
  b. adding to step a. varying concentrations of an antimicrobial agent, thereby creating a plurality of suspensions comprising a combination of bacteria and antimicrobial agent,
  c. incubating the plurality of suspensions comprising a combination of bacteria and antimicrobial agent of step b. at a suitable temperature for a suitable period of time, thereby creating a plurality of incubated suspensions comprising a combination of bacteria and antimicrobial agent,
  d. adding to the new suspensions of step c., a single membrane-associated dye,
  e. illuminating the new suspensions of step d. with an incident light at one or more excitation wavelengths,
  f. measuring intensity of emitted light at two emission wavelengths of each suspension,
  g. determining the spectral intensity ratios based upon step f. of each suspension, and h. determining the minimum inhibitory concentration based upon step g. by determining the spectral intensity ratio (SIR) as a function of the antimicrobial concentration.

The function of step h can be a step function is in the form of:

$$y(x) = a \cdot \text{erf}\left(\frac{b\pi(x-c)}{2}\right)$$

wherein a is a scaling parameter, b determines the step slope and c is the MIC value.

The method can include the single membrane-associated dye which is a styryl dye or a cyanine dye, which can be FM 1-43.

The method can include the one excitation wavelength which is a wavelength selected between the range of 360 nm and 570 nm.

The method can include the one emission wavelength which is a wavelength selected between the range of 520 nm and 850 nm.

The method can include the sample which is a bodily fluid, such as blood, urine, or a clinical isolate.

The method can include the suitable incubation temperature which is between 35° C. and 40° C.

The method can include the suitable period of incubation time which is between 30 minutes and 5 hours.

The method can include varying concentrations of an antimicrobial agent. By varying concentrations of an antimicrobial agent it is meant that the antimicrobial agent is prepared by serial dilutions.

The method can include the sample is initially filtered to isolate the bacteria in a concentrated form and is then diluted to a fixed concentration of bacteria.

The method can include the sample is initially concentrated via centrifugation or filtering and then diluted to a fixed concentration of bacteria.

The method can include the dilution occurs with a liquid growth medium.

The method can include removing a portion of each of the plurality of incubated suspensions comprising a combination of bacteria and antimicrobial agent and placing the portions in new receptacles after step c.

The method can include the function of step h is a step function.

The present invention also includes a second method for determining whether bacteria in a sample is susceptible, resistant, or intermediate to antimicrobial treatment comprising the steps of:

a. preparing a plurality of bacterial suspensions in a plurality of receptacles, b. adding to step a. varying concentrations of an antimicrobial agent, thereby creating a plurality of suspensions comprising a combination of bacteria and antimicrobial agent, c. incubating the plurality of suspensions comprising a combination of bacteria and antimicrobial agent of step b. at a suitable temperature for a suitable period of time, thereby creating a plurality of incubated suspensions comprising a combination of bacteria and antimicrobial agent, d. adding to the suspensions of step c. a single membrane-associated dye, e. illuminating the suspensions of step d. with an incident light at one or more excitation wavelengths, f. measuring intensity of emitted light at one emission wavelength, g. determining the spectral intensity ratios based upon step f., and h. determining whether bacteria in the sample is susceptible, resistant, or intermediate to antimicrobial treatment based upon step g. by determining the spectral intensity ratio (SIR) as a function of the antimicrobial concentration; the second method can include the step of removing a portion of each of the plurality of incubated suspensions comprising a combination of bacterial and antimicrobial agent and placing the portions in new receptacles after step c.

The second method can include the function of step h is a step function.

The illumination step e in both the first and second methods can be at two or more wavelengths. The measuring step of the first and second step can be accomplished by a cytometer.

BRIEF DESCRIPTION OF THE DRAWINGS

FIGS. 4, 6, and 11 show that the y axes are normalized SIRS wherein the SIR readings are normally between −1 and 1 to make an easier calculation of the error function based upon the SIR data.

DESCRIPTION OF THE INVENTION

Figure 1:
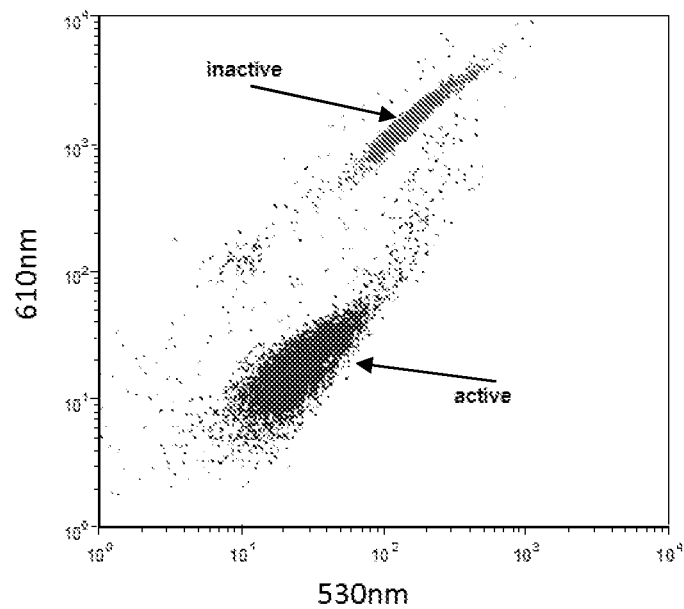
FIG. 1 shows a flow cytometer scatter plot of active (labeled as active) and inactive E. coli (labeled as inactive)
Figure 2:
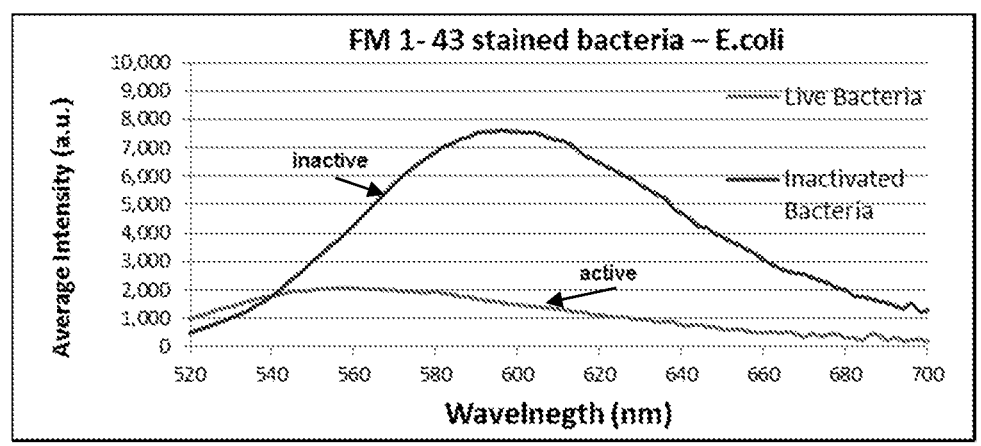
FIG. 2 shows the fluorescence spectrum of active and inactive E. coli stained with FM 1-43 dye.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about." In this manner, slight variations above and below the stated ranges can be used to achieve substantially the same results as values within the ranges. Also, unless indicated otherwise, the disclosure of ranges is intended as a continuous range including every value between the minimum and maximum values. As used herein, "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including, but not limited to, human beings, and "mammal" refers to all mammals, including, but not limited to, human beings.

As used herein, the term "sample" refers to a material to be tested or analyzed. The sample contains bacteria and may be obtained from various sources. For instance, the sample to be analyzed may be a liquid, semi-liquid, or dry sample. The sample may be obtained from drinking water, a food or a beverage, a pharmaceutical product, a personal care product, or a body fluid. Samples may be obtained from a municipal water system, a well, potable water, waste water, a natural water source, recreational water, or a soil. In different embodiments, samples are obtained from medical devices. Examples of medical devices include, but are not limited to, implants, patches and heart valves. In other instances, samples may be obtained from bodily fluids. These may include, but are not limited to, blood or plasma, saliva, urine, throat sample, or gastrointestinal fluid (these may also be referred to as "biological sample"). "Samples" may also refer to clinical isolates. Clinical isolates may, in some instances, refer to bacteria that was isolated from bodily fluids and stored by suitable laboratory means. In general, clinical isolates refer to isolated bacteria. Therefore, in short, the term "sample" most broadly refers to the presence (or speculated presence) of bacteria. In some instances, the sample may be bacteria isolated from a source (such as a clinical isolate), whereas in other instances the sample may refer to a substance carrying bacteria/microbial agents (such as blood, urine, water, etc.).

As used herein, the terms "bacteria" (bacterial or bacterium) and "microbe" (microbial) refer to the same thing. That is, they refer to single-cell, prokaryotic, microorganisms, they are small, usually rod or cocci shaped, and may be disease causing. Bacteria-causing diseases are typically treated with antibiotics. Additionally, "bacterial strain" or "bacterial isolates," refer to the same thing. Further, as recited herein "clinical isolate" refers to the same thing as a "bacterial isolate." That is, a strain/isolate is a genetic variant, or subtype, of a bacterium. In other words, one type of bacterial species may contain several different strains. The strains differ based on genetic mutations, such as through acquisition of additional genes, such as antibiotic-resistance genes, etc. These terms would be understood by a person of ordinary skill in the art.

As used herein, the terms "antibacterial" and "antimicrobial" refer to the same thing. That is, they refer to anything that is capable of killing and/or inactivating a bacterial or microbial organism.

As used herein, "live cell," "live bacteria," or "active bacteria" means a bacterial cell which has the potential to grow and divide. "Dead" and "inactivated" are used interchangeably to refer to dead bacterial cells. Regarding FIGS. 1, 3, 5, 7, 9, and 10, the lighter dots or lines represent active cells and the darker dots or lines represent inactive cells (noted as such in the figures).

As used herein, the "treatment" or "treating" of a wound, defect, infection, or the like means administration to a patient by any suitable dosage regimen, procedure and/or administration route an amount of a composition, device or structure effective to, and with the object of achieving a desirable clinical/medical endpoint, including attracting progenitor cells, healing a wound, correcting a defect, etc.

As used herein, "dosage regimen" means the schedule of doses of a therapeutic agent at a particular concentration, per unit of time, including the time between doses (e.g., every 6 hours) or the time when the dose(s) are to be given (e.g., at 8 a.m. and 4 p.m. daily), and the amount (that is, the concentration) of a medicine to be given at each specific time.

A "therapeutically effective amount" refers to an amount effective, at dosages and for periods of time necessary, to achieve the desired therapeutic result. An "amount effective" for treatment of a condition is an amount of an active agent or dosage form, such as the coacervate composition described herein, effective to achieve a determinable endpoint. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount of a drug or dosage regimen may vary according to factors such as the disease state, age, sex, weight of the individual, and the ability of drug or dosage regimen to elicit a desired response in the individual. A therapeutically effective amount is also one in which any toxic or detrimental effects of drug or dosage regimen are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc. be proportionally reduced or increased as indicated by the exigencies of the therapeutic situation. In some instances, it may be especially advantageous to formulate parenteral compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In some instances, as provided herein, a dosage regimen may mean the administration of one or more antibiotics and a specific concentration and at specific times to a patient in need thereof.

Fluorescence spectroscopy has been extensively exploited for studies of molecular structure and function in chemistry and biochemistry. However, its effectiveness in microbial identification and characterization has only been recently recognized in the last two decades.

Briefly, as would be appreciated by one of ordinary skill in the art, fluorescence spectroscopy refers to a type of electromagnetic spectroscopy that analyzes fluorescence from a sample. It involves using a beam of light (for instance, ultraviolet light) that excites the electrons in molecules of certain compounds and causes them to emit light; typically, but not necessarily, visible light.

Provided herein are methods that exploit fluorescence spectroscopy allowing for the detection of live bacteria compared to dead bacteria, and further allowing for the determination of the minimum concentration needed for an antibiotic to inhibit bacterial activity.

Specifically, provided herein is a method for: identifying a type of bacterial microorganism from a sample; determining the effectiveness of a dosage regimen; and determining the minimum inhibitory concentration of a dosage regimen. In general, the steps include: obtaining a sample containing bacteria; preparing a set of test tubes or 96 well plates (first receptacles) containing the sample; incubating the test tubes or plates containing the sample with a range of varying concentrations (such as, by serial dilutions) of an antimicrobial agent at a suitable temperature (such as, between 30° C. and 50° C., between 35° C. and 40° C., or around 37° C.) for a given amount of time (for instance, between 30 minutes and 5 hours or between 2 hours and 4 hours); after incubation transferring a portion of the incubated samples to optical cups or cuvettes (second, or new, receptacles); adding a suitable fluorescence dye to the tubes/plates; the tubes/plates are then subjected to an optical analysis, wherein the optical analysis includes a flow cytometer, and wherein the optical analysis includes exciting the fluid sample with different wavelengths, collecting, and detecting the fluorescent emissions; determining the ratio of intensity of emissions from at least two wavelengths, and thereby determining the ratio of live bacteria to dead bacteria; and based upon the ratio determining the minimum inhibitory concentration.

In some instances, where the sample is, for example, a bodily fluid, the method may first include the following steps: 1) obtaining the bodily fluid sample, 2) centrifuging the sample (for example, 15 minutes at 24×g), and 3) diluting the supernatant with a suitable broth (for example, Cation-Adjusted Mueller Hinton Broth (CAMHB)).

In some instances, where the sample is, for example, a clinical isolate. The method may first include the following steps: 1) obtaining the clinical isolate; 2) streaking the clinical isolate on agar plates containing a suitable growth medium (e.g., blood agar plates); 3) incubating the plates overnight at 37° C.; 4) picking single colonies and suspending them in a suitable buffered solution (for example, phosphate buffered saline), and adjusting the number of bacteria to a 0.5 McFarland standard.

The methods provided herein, in some instances, rely on serial dilutions in order to determine the minimum concentration needed for a specific antimicrobial agent to inactivate a given microbe. Serial dilution is well-known in the art and generally refers to the stepwise dilution of a substance in solution. Usually the dilution factor at each step is constant, resulting in a geometric progression of the concentration in a logarithmic fashion. As provided herein, serial dilutions of the antimicrobial agent permits the testing of a range of concentrations of the antimicrobial agent in order to determine if the antimicrobial agent is effective in inactivating the microbe and, if so, the minimum concentration needed to inactivate the microbe.

As provided herein, the given concentration of an antimicrobial agent may vary from microbe to microbe (if known), antimicrobial agent to antimicrobial agent, the presence of resistance genes in the microbe, or any other factors. The concentration of the antimicrobial agent at each step of the serial dilution will vary based upon these factors, and others, and is not meant to be a limiting feature. For instance, the concentration of the antimicrobial agent may range from 0 µg/ml to 5 mg/ml, and all subranges therebetween inclusive. One example range of concentration of the antimicrobial may for instance be: 0 (control sample), 0.5 µg/ml, 1 µg/ml, 2 µg/ml, 4 µg/ml, 8 µg/ml, 16 µg/ml, 32 µg/ml, 64 µg/ml, 128 µg/ml, 256 µg/ml, and all subranges therebetween inclusive. Also, diluting can be greater than 256 µg/ml.

The method additionally may include a dye. For instance, upon staining bacteria with fluorescent membrane dyes, such as a styryl dye, the emission fluorescence of live bacteria versus inactive bacteria are weaker and shifted. Such phenomena might be the result of the interaction of the dyes in the lipophilic membrane environment in the live cells versus the inactive cells where the dyes are inserted to the more hydrophilic environment of the cytoplasm.

Dyes include, but are not limited to, fluorescent dyes which incorporate into the lipid bilayer. Examples of fluorescent dyes include styryl dyes and cyanine dyes. Representative styryl dyes include FM® 1-43, FM® 1-43FX, FM® 4-64 and FM® 4-64FX, FM® 2-10 dye. Representative cyanine dyes include Cy2, Cy3, Cy3B, Cy3.5, Cy5, Cy5.5 and Cy7. FM 1-43 is N-(3-Triethylammoniumpropyl)-4-(4-(Dibutylamino)Styryl)Pyridinium Dibromide, purchased from Life Technology (#T-35356), and also sold by Sigma as "Synaptogreen" (#S6814). FM 4-64 is N-(3-Triethylammoniumpropyl)-4-(6-(4-(Diethylamino) Phenyl) Hexatrienyl) Pyridinium Dibromide purchased from Life Technology (#T-13320) or Sigma as "Synaptored" (#S6689). FM 4-64 is a gram positive dye and is also known as Synaptored.

More than one dye can be used, but the present method may be performed with a single dye. The use of a single dye not only simplifies the method, but reduces variability caused by the presence of two dyes.

Provided herein, in some instances, are methods for differentiating and comparing live bacteria from inactive bacteria. The method is performed using spectral intensity ratio analysis (SIR). SIR measures the intensity of emitted light after excitation at two wavelengths, and obtaining the ratio of the emitted light between the two wavelengths. Specifically, upon excitation of a specimen at a specific wavelength, measurable differences are evident in both the maximum emission peak and emission intensity between live and inactive bacteria. Accordingly, the ratio of emission intensities at two designated wavelengths or spectral intensity ratio can be used as a means of differentiating live bacteria from inactive bacteria. It is believed that use of SIR does not depend on the amount of dye used and the number of cells because SIR relies on a ratio of intensities.

More specifically, the spectral intensity ratio (SIR) maybe determined as follows:

$$SIR = \frac{I_{\lambda 2}}{I_{\lambda 1}} = \frac{I2}{I1}$$

where $I_{\lambda 1}=I1=$an emission intensity at a first wavelength, and
where $I_{\lambda 2}=I2=$an emission intensity at a second wavelength, for example $$SIR = \frac{I_{\lambda=610}}{I_{\lambda=530}}$$

Where "I" (intensity of emission) is the mean value of the scatter plot at each wavelength.

In this case, $I_{\lambda=610}$ is the intensity at the 610 nm wavelength, and $I_{\lambda=530}$ is the intensity at the 530 nm wavelength. $I2=I_{\lambda=610}$ and $I1=I_{\lambda=530}$ is preferable for Gram Negative bacteria. Low SIR values correspond to active bacterium population, while high values show a larger inactive bacterium population. The $I_\lambda$ may be at other wavelengths specifically for Gram Positive bacteria, wherein $I2=I_{\lambda=780}$ and $I1=I_{\lambda=670}$, wherein $I2=780$ nm and $I1=670$ nm. Also, the Gram Positive dyed bacteria may be illuminated at the one wavelength, for example, 488 nm, or two wavelengths, for example, 488 nm and 532 nm. An appropriate dye is used for Gram Positive bacteria.

The method of the present invention, as noted above, may include removing a portion of sample after incubation, transferring the portion of the incubated sample having different concentrations of an antimicrobial agent to cuvettes; adding a suitable fluorescence dye to the cuvettes; and then subjecting samples contained in the cuvettes to an optical analysis to obtain SIR. However, in some instances, the dye and measurements may be placed directly in the diluted sample having different concentrations of microbial agents after incubation with the one microbial agent. The method of the present invention allows accurate and rapid differentiation of live from inactive cells through relying on excitation/emission at a single bacteria level-based analysis rather than culture based validation, as well as requiring the use of only one dye to successfully differentiate. Thus, as noted above, the method in some instances may include the steps of: staining the sample with a single membrane-associated dye; illuminating the sample with an incident light at excitation; measuring, for each bacterial cell (i) the intensity I1 of emitted light at wavelength $\lambda 1$; and (ii) the intensity I2 of emitted light at wavelength $\lambda 2$; and calculating a ratio I2/I1. In one embodiment this may be done on a single cell and in another embodiment, this same process may be conducted for more than one cell. In further such embodiments, bulk intensity may be measured to determine whether the sample contains live or inactive bacteria. As noted above, optical analysis may be done in a separate tube from the original tube used for incubation. Also, although the excitation wavelength is preferably at 488 nm for the specimen for Gram Negative bacteria and 488 or 532 nm for Gram Positive bacteria, others excitation wavelengths may be used.

The system to perform the method of the invention is preferably a device capable of excitation of the membrane-associated dye and measuring emission intensity at the prescribed wavelengths $\lambda 1$ and $\lambda 2$, such as (but not limited) to a flow cytometer, fluorescent microscope, or other instrument capable of fluorescence analysis.

The emission spectrum profile is measured with a spectral analyzer or emission filters. The excitation wavelength is between about 360 nm and about 600 nm and the wavelengths at which I1 and I2 are measured are between about 520 nm and about 800 nm. In one embodiment, for the dye FM 1-43, the excitation wavelength is 488 nm and the emission wavelengths at which I1 and I2 are measured are 530 nm and 610 nm, respectively. For the dye FM 4-64, the excitation wavelength could be in between 488 to 570 nm and the emission wavelengths at which I1 and I2 are measured are 670 nm and 780 nm, respectively.

Flow cytometry (FCM) is testing a single cell at a time, therefore it enables the detection of the antibiotic effect on a single bacteria level and not as a whole group effect, such as growth curve. By measuring a large number of the bacterial population, in a single test, on the two emission wavelength channels in the FCM, it can be determined whether the antimicrobial treatment is successful in its initial stage of changes in the bacteria statehood. FIG. 1 is a fluorescence dot plot that shows the flow cytometric fluorescence measurement of active and inactive bacteria. As can be seen from the figure, using two wavelengths channels (530 nm and 610 nm) enables distinguishing between active and inactive bacteria. Spectral intensity ratio (SIR) calculation is done by dividing the mean fluorescence value of the 610 nm channel by the mean fluorescence value of the 530 nm channel. Typical values of SIR for active bacteria are between 0.7 and 2, while the values for inactive bacteria are higher (>2.5).

In some embodiments, the sample may be analyzed for success or failure of a bacterial inactivation treatment, such as (but not limited to) antibiotic or antibacterial treatment (also referred to herein as antimicrobial agent), chlorine inactivation, heating, ethanol, and UV irradiation by medium pressure. In further embodiments, a threshold value can be determined by taking the I2/I1 of a pretreatment sample and then compared to the I2/I1 of the sample to determine efficacy of the bacterial inactivation treatment.

As recited herein, "minimum inhibitory concentration" or "MIC" refers to the lowest concentration of an antimicrobial (for example, an antibiotic) drug that will inhibit the visible growth of a microorganism after overnight incubation. It is believed that the specimens will have to be incubated in cultured media before the process to ensure an appropriate number of cells for the test.

As provided herein, MIC is calculated by plotting the SIR as a function of the antimicrobial concentration and approximating it to a step function, for example, in the form of:

$$y(x) = a \cdot \text{erf}\left(\frac{b\pi(x-c)}{2}\right)$$

Where a, b and c are parameters and erf is the error function. The MIC is the value of the parameter c.

Other suitable functions may be used, for instance the tan h function. SIRS for different concentrations as shown in the MIC graphs (see, for example, FIG. 11), a, b, and c are determined on a case-by-case basis Bacteria may include, but are not limited to, Gram Negative bacteria and Gram Positive bacteria, such as coliform bacteria, enterobacteria, *Salmonella, Listeria, Shigella, Pseudomonas, Staphylococcus* or *Methanobacterium*. For instance, *Escherichia coli, Klebsiella pneumonia, Acinetobacter, Proteus mirabilis, Enterococcus cloacae, Aeromonass, Klebsiella oxytoca, Enterobacter cloacae, Proteus mirabilis*, and *Citrobacter freundii*.

Antibiotics (or antimicrobial agents) may include, but are not limited to, ampicillin, gentamicin, quinolones (e.g., ciprofloxacin), amoxicillin, carbapenems (e.g., imipenem), tetracyclines, chloramphenicol, ticarcillin, bactrim, etc.

In some aspects, the sample is initially filtered to isolate the bacteria in a concentrated form and is then diluted to a fixed concentration of bacteria. In other aspects, the sample is initially concentrated via centrifugation and then diluted to a fixed concentration of bacteria. Dilution of the concentrated bacteria may occur in a suitable medium, such as liquid growth medium.

The present invention is more particularly described in the examples that follow, which are intended to be illustrative only.

EXAMPLES

Example 1

In this example, a rapid method for AST and MIC determination directly from blood culture with a turnaround time of 15 mins after 2-4 hours of antibiotics exposure is presented.

Materials and Methods:

In general, the method includes; blood culture centrifugation, bacterial antimicrobial exposure for 2 to 4 hours, bacteria staining with a single fluorescence dye followed by a flow cytometric measurement, and mathematical analysis.

Sample Preparation—Macro Dilution Method 31 positive blood cultures were obtained from Sheba Medical Center (Ramat-Gan, Israel) and tested for antimicrobial susceptibility with gentamicin and ampicillin antibiotics (Sigma-Aldrich, USA). A total of 62 positive blood samples-antibiotics combinations were tested.

a) Positive blood samples were received from Sheba Medical Center, 2 ml of each sample were centrifuged for 15 min at 24×g and Supernatants were diluted 1:1000 with Cation-Adjusted Mueller Hinton Broth (CAMHB).
b) Antimicrobial stock solutions were prepared according to CLSI recommendations, and were diluted in CAMHB, to a concentration which was 2 fold higher from the highest concentration recommended for each antimicrobial combination ("Class II Special Controls Guidance Document: Antimicrobial Susceptibility Test (AST) Systems", Aug. 28, 2009, FDA).
c) For each sample/antimicrobial combination, a set of tubes was prepared for which 1 ml of CAMHB medium was added, except for the first tube.
d) To each first tube of the set, 2 ml from the antimicrobial stock solution (b) was dispensed.
e) From the first tube a serial dilutions of 2 folds were prepared by transferring 1 ml of the solution to the next tube until the lowest required concentration by CLSI. 1 ml was discarded from the last tube in each set of tubes.
f) To each tube in the set, 1 ml of bacterial sample solution (a) was added.
g) For each serial dilutions set, two controls were added. As a negative control, a tube with 2 ml of CAMHB. As a positive control, a tube with bacterial sample solution (a) without antimicrobial agent.
h) All tubes were incubated at 37° C.
i) 2-4 hours from incubation initiation, 200 μl from each tube were transferred into a fresh tube, dyed with 2 μl of Synaptogreen or FM 1-43 (Sigma-Aldrich; Molecular Probes, respectively) and measured by a flow cytometer. The rest of the sample was further incubated for 16-20 hours and then was visually evaluated for growth.

Data Interpretation:

In order to quantify the influence of a certain antimicrobial exposure we define the spectral intensity ratio (SIR) as follows:

$$\text{spectral intensity ratio } (SIR) = \frac{I_{\lambda=610}}{I_{\lambda=530}}$$

Where (I) is the mean value of the scatter plot at each wavelength. Low spectral intensity ratio (SIR) values correspond to active bacterium population, while high values show a larger inactive bacterium population. The main advantage of using a single dye and the above spectral intensity ratio (SIR) is the elimination of the result dependency on the dye concentration and optical efficiency.

The MIC is calculated by plotting the spectral intensity ratio (SIR) as a function of the antimicrobial concentration and approximating it to a step function in the form of $$y(x) = a \cdot \text{erf}\left(\frac{b\pi(x-c)}{2}\right)$$

Where a, b, and c are parameters and erf is the error function. The parameters are used to approximate the measured SIR to a step function; a is a scaling parameter, b determines the step slope, and c is the MIC value The SIR values are used to determine the erf parameters by a best fit approximation.

Results:

62 samples (31 positive blood cultures and 2 antibiotics combination) were analyzed in triplicates. Each sample was measured by the flow cytometer and the MIC was calculated using the spectral intensity ratio (SIR) calculation and step function estimation. The bacteria identified within the samples were; *E. coli* (15 samples), *K. pneumonia* (6 samples), *A. baummanii* (4 samples), *P. mirabilis* (2 samples), *E. cloacae* (2 samples), *Aeromonass* spp. (1 sample), and *K. oxytoca* (1 sample).

Figure 3:
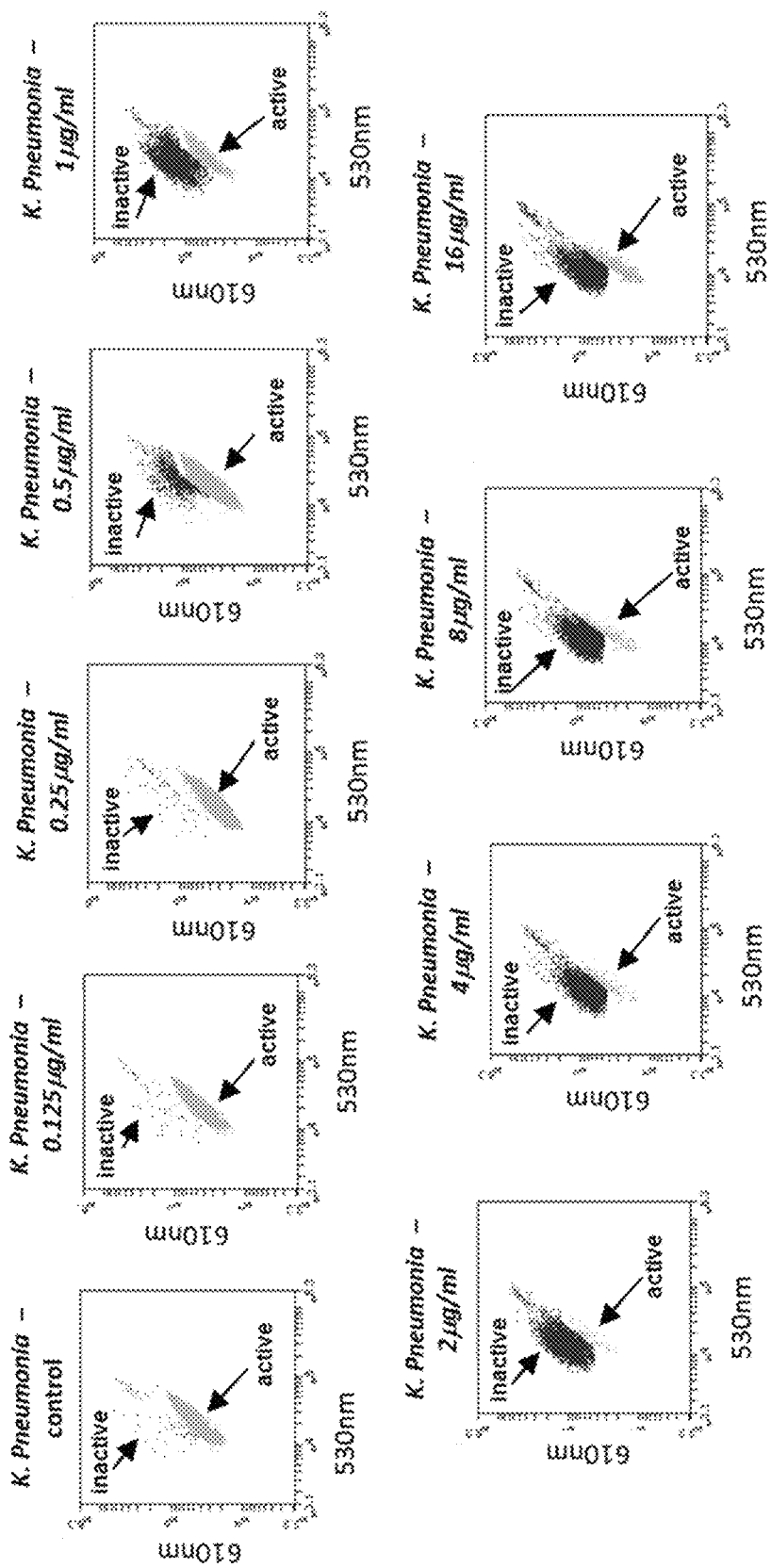
FIG. 3 shows a two wavelength fluorescence scatter plot of K. pneumonia exposed to gentamicin (area noted as active depicts active K. pneumonia population and area noted as inactive depicts inactive K. pneumonia population)
Figure 4:
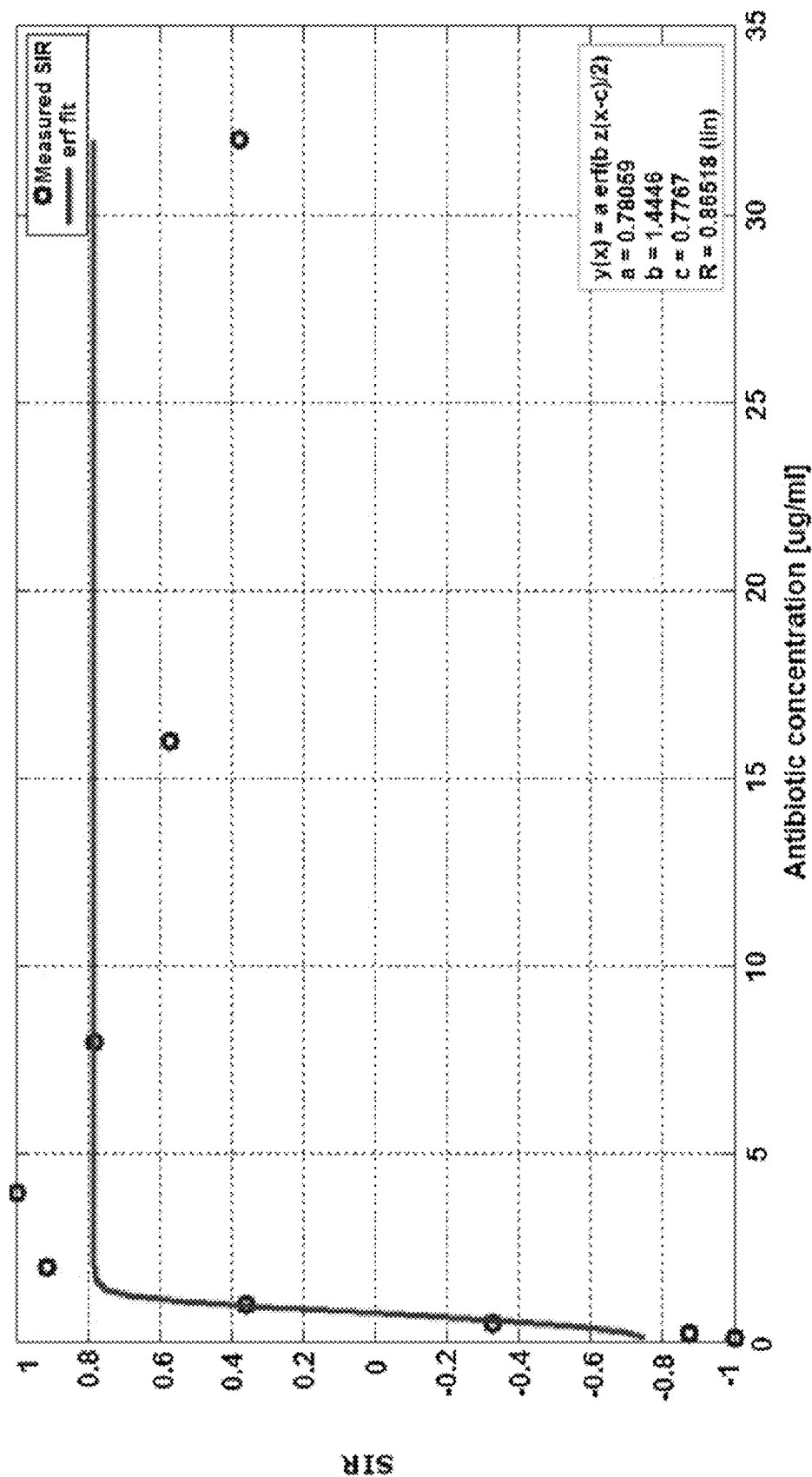
FIG. 4 shows spectral intensity ratio (SIR) as a function of antibiotic concentration for K. pneumonia exposed to gentamicin (circles note measured spectral intensity ratio (SIR) and solid line depicts approximated step function)
Figure 5:
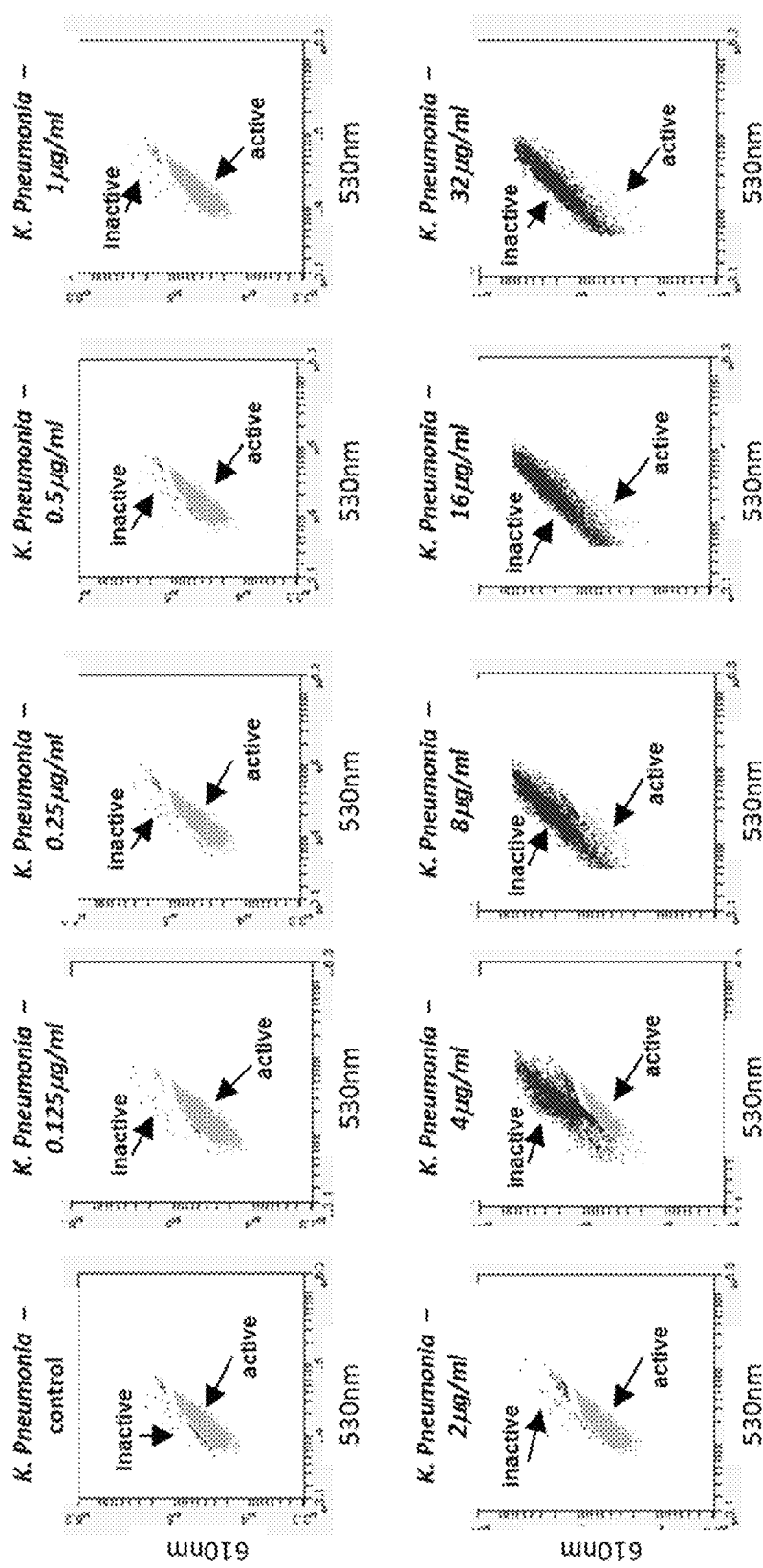
FIG. 5 shows a two wavelength fluorescence scatter plot of K. pneumonia exposed to ampicillin (area noted as active depicts active K. pneumonia population and area noted as inactive depicts inactive K. pneumonia population)

FIG. 3 shows fluorescence scatter plots (typical flow cytometric measurements) of *K. pneumonia* treated with gentamicin. As can be seen from the figure, as long as the antibiotics concentration is below the MIC, the majority of the bacterium population is active (area noted as active in the scatter plot). Once the antibiotic concentration reaches the MIC, the inactive bacterium population increases significantly (area noted as inactive in the scatter plot). The increase in the inactive bacterium population increases the spectral intensity ratio (SIR) as can be seen in FIG. 4. The spectral intensity ratio (SIR) as a function of antibiotic concentration is approximated to a step function (solid line in FIG. 4) and the MIC is determined to be 1 µg/ml.

Figure 6:
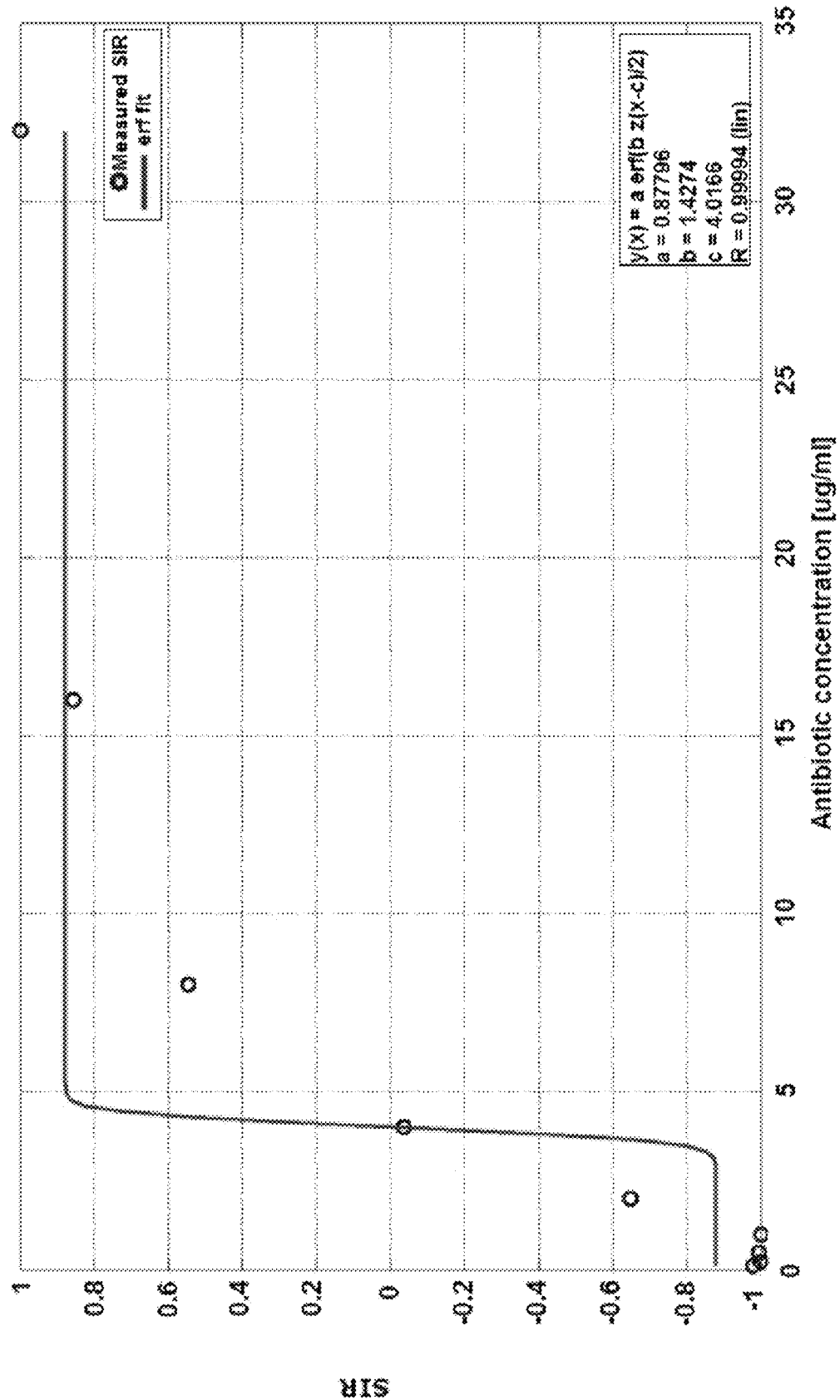
FIG. 6 shows spectral intensity ratio (SIR) as a function of antibiotic concentration for K. pneumonia exposed to ampicillin (circles note measured spectral intensity ratio (SIR) and solid line depicts approximated step function)

Similar results (FIGS. 5 and 6) were obtained for *K. pneumonia* and ampicillin. This time the MIC was found to be 4 µg/ml.

Figure 7:
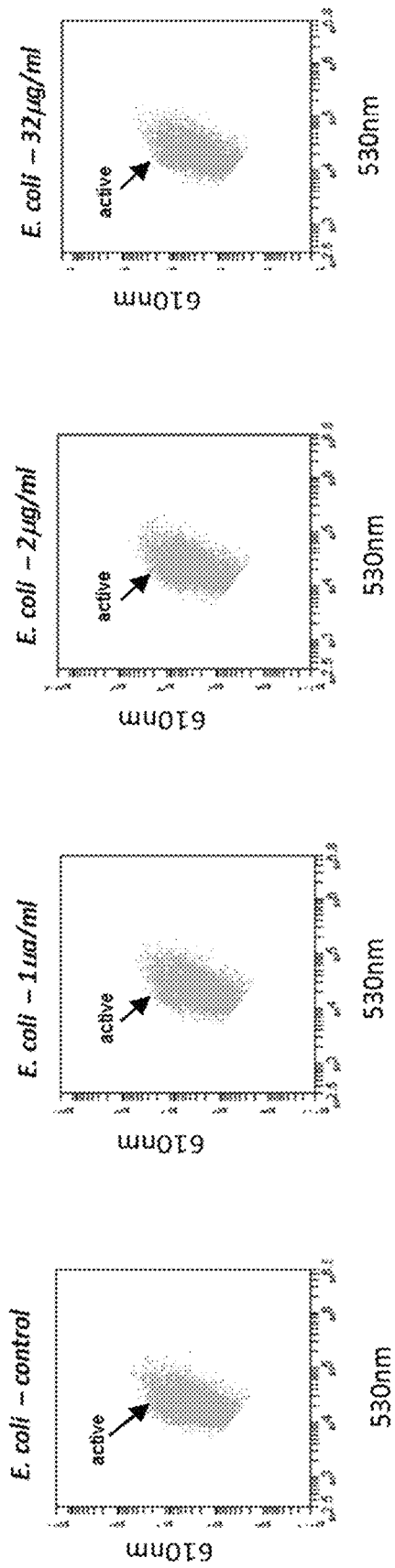
FIG. 7 shows a two wavelength fluorescence scatter plot of E. coli exposed to ampicillin.
Figure 8:
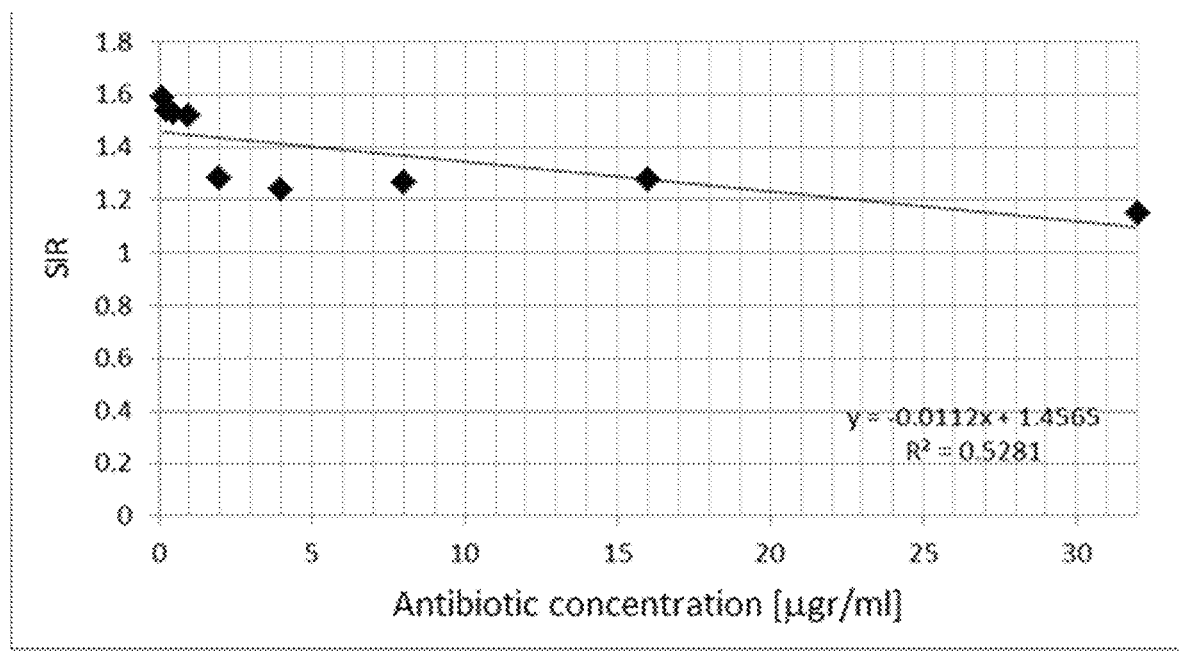
FIG. 8 shows spectral intensity ratio (SIR) as a function of antibiotic concentration of E. coli resistant to ampicillin treatment.

An example of a strain, *E. coli*, which was found to be resistant to ampicillin is presented in the FIGS. 7 and 8. As can be seen from FIG. 7, the flow cytometry fluorescence scatter plot remains practically the same even at high antibiotic concentrations. This is reflected in the spectral intensity ratio (SIR) (FIG. 8), where the slope is negative and small.

The following tables summarize the performance of the method in this study. It has a 98.4% (61/62) essential agreement (the MIC result is within ±1 antibiotic dilution from the reference method) and 100% categorical agreement ("Class II Special Controls Guidance Document: Antimicrobial Susceptibility Test (AST) Systems," Aug. 28, 2009, FDA).

Tables 1 and 2 present the results of the positive blood sample experiment using the macro dilution as the reference method. As can be seen from Table 1, the essential agreement is 98.4% and categorical agreement is 100%. There are no errors as defined by "Class II Special Controls Guidance Document: Antimicrobial Susceptibility Test (AST) Systems," Aug. 28, 2009, FDA.

Table 2 presents the method accuracy by showing how many samples were the same MIC value as the reference method, and how many deviated from the MIC value of the reference method and by how many dilutions. As can be seen from Table 2, the majority of the results are within +/−1 of the MIC value, which is an acceptable result by the FDA.

Example 2

In this Example, a rapid method for AST and MIC determination from clinical isolates.

Materials and Methods:

Our method includes bacterial antimicrobial treatment for 2 to 4 hours, bacteria staining with a single fluorescence dye followed by a flow cytometric measurement, and mathematical analysis. The following paragraphs describe the method in details.

Sample Preparation—Macro Dilution Method:

Thirty (30) clinical isolates of *E. coli, K. pneumoniae, E. cloacae, P. mirabilis*, and *C. freundii*, purchased from JMI Labs (IA, USA), were tested for antimicrobial susceptibility with gentamicin, ampicillin, and ciprofloxacin antibiotics (Sigma-Aldrich, USA). A total of 90 isolates-antibiotics combinations were tested.

a) All strains were cultured onto 5% sheep blood agar (Hylabs, Israel), following overnight incubation, colonies were harvested and suspended in Phosphate Buffer Saline (PBS, Sigma-Aldrich). Each bacterial solution was then adjusted to 0.5 McFarland standard (~$1.5 \times 10^8$ CFU/ml).

b) The adjusted bacterial suspensions were diluted 1:100 with Cation-Adjusted Mueller Hinton Broth (CAMHB, Hylabs Israel) to a concentration of ~$1 \times 10^6$ CFU/ml.

c) Antimicrobial stock solutions were prepared in CAMHB according to CLSI recommendations starting at concentration which was 2 fold higher from the highest concentration of each bacterium/antimicrobial combination ("Performance Standards for Antimicrobial Susceptibility Testing", M100-S17, V. 27, No. 1, CLSI).

TABLE 1

Results analysis

| Antimicrobial agent | No. of Strains | Reference Method Susceptibilities | | | Essential Agreement | | Categorical Agreement | | Minor error | | Major error | | Very major error | |
|---|---|---|---|---|---|---|---|---|---|---|---|---|---|---|
| | | S | I | R | No. | % | No. | % | No. | % | No. | % | No | % |
| Ampicillin | 31 | 5 | 0 | 26 | 31 | 100.0% | 31 | 100.0% | 0 | 0.0% | 0 | 0.0% | 0 | 0.0% |
| Gentamicin | 31 | 21 | 0 | 10 | 30 | 96.8% | 31 | 100.0% | 0 | 0.0% | 0 | 0.0% | 0 | 0.0% |
| Total | | | | | | 98.4% | | 100.0% | | 0.0% | | 0.0% | | 0.0% |

TABLE 2

MIC Agreement

| Antimicrobial agent | Range µg/ml | Essential agreement [%] | Deviation from MIC | | | | | | | | | | | |
|---|---|---|---|---|---|---|---|---|---|---|---|---|---|---|
| | | | ≤−5 | −4 | −3 | −2 | −1 | 0 | 1 | 2 | 3 | 4 | ≥5 | total |
| Ampicillin | 0.125-32 | 100.0% | 0.0% | 0.0% | 0.0% | 0.0% | 12.9% | 87.1% | 0.0% | 0.0% | 0.0% | 0.0% | 0.0% | 100.0% |
| Gentamicin | 0.125-32 | 96.8% | 0.0% | 0.0% | 0.0% | 3.2% | 22.6% | 48.4% | 25.8% | 0.0% | 0.0% | 0.0% | 0.0% | 100.0% |

This study shows that antibiotic susceptibility testing for positive blood samples can be conducted using a single dye stain and flow cytometry measurement. By defining the spectral intensity ratio (SIR) parameter and plotting it as a function of the antibiotic concentration, it is possible to determine the bacteria MICs and whether it is susceptible, intermediate, or resistant to a certain antibiotic directly from positive blood samples. The spectral intensity ratio (SIR) method is done within 15 minutes following 2-4 hours of antibiotic exposure.

d) For each bacterium/antimicrobial combination, a set of tubes was prepared for which 1 ml of CAMHB medium was added, except for the first tube.

e) To each first tube of the set 2 ml from the antimicrobial stock solution (c) was dispensed.

f) From the first tube a serial dilutions of two-fold dilutions were prepared by transferring 1 ml of the solution to the next tube until the lowest required concentration by CLSI for each bacterium/antimicrobial combination. 1 ml was discarded from the last tube in each set of tubes.

g) For each serial dilutions set, two controls were added. As a negative control, a tube with 2 ml of CAMHB. As a positive control, a tube with bacterial inoculum without antimicrobial agent.
h) To each tube in the set, 1 ml of bacterial solution (b) was added which resulted in a final inoculum concentration of about $5 \times 10^5$ CFU/mL.
i) All tubes were incubated at 37° C.
j) 2-4 hours from incubation initiation, 200 μl from each tube were transferred into a fresh tube, dyed with 2 μl of Synaptogreen or FM 1-43 (Sigma-Aldrich; Molecular Probes, respectively) and measured by a flow cytometer. The rest of the sample was further incubated for 16-20 hours and then was visually evaluated for growth.

Data Interpretation:

In order to quantify the influence of a certain antimicrobial treatment, we define the spectral intensity ratio (SIR) as follows:

$$\text{spectral intensity ratio } (SIR) = \frac{I_{\lambda=610}}{I_{\lambda=530}}$$

Where (I) is the mean value of the scatter plot at each wavelength.

Low spectral intensity ratio (SIR) values correspond to active bacterium population, while high values show a larger inactivate bacterial population. The main advantage of using a single dye and the above spectral intensity ratio (SIR) is the elimination of the result dependency on the dye concentration and optical efficiency.

The MIC is calculated by plotting the spectral intensity ratio (SIR) as a function of the antimicrobial concentration and approximating it to a step function in the form of $$y(x) = a \cdot \text{erf}\left(\frac{b\pi(x-c)}{2}\right)$$

Where a, b, and c are parameters and erf is the error function. The parameters are used to approximate the measured SIR to a step function; a is a scaling parameter, b determines the step slope, and c is the MIC value. The SIR values are used to determine the erf parameters by a best fit approximation.

Results:

Ninety (90) samples (30 strains and 3 antibiotic combinations) were analyzed in triplicate. Each sample was measured by the flow cytometer and the MIC was calculated using the spectral intensity ratio (SIR) calculation and step function estimation.

Figure 9:
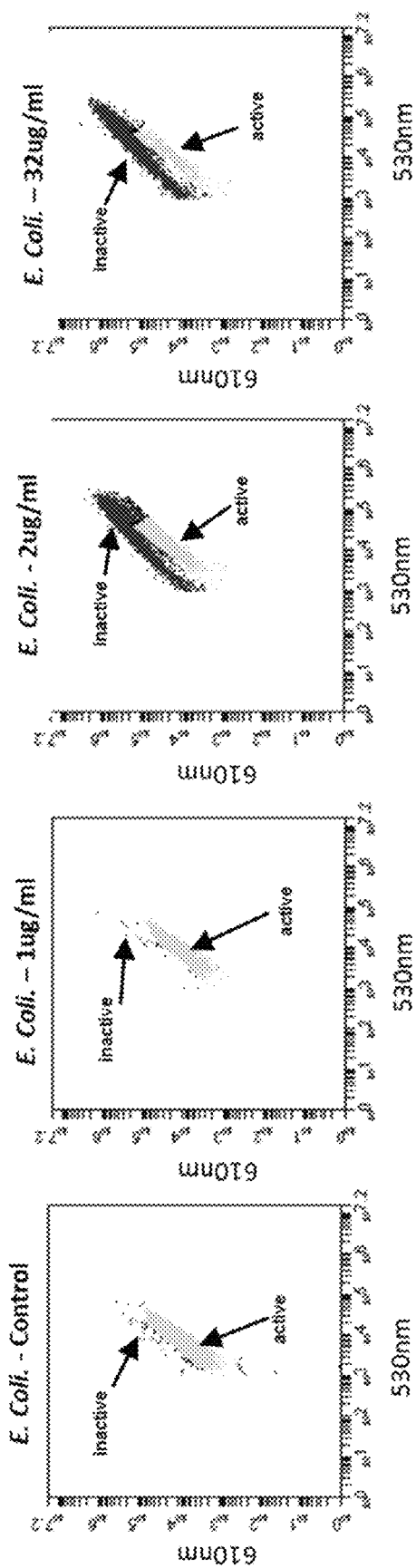
FIG. 9 shows a two wavelength fluorescence scatter plot of E. coli exposed to gentamicin (area noted as active depicts active E. coli population and area noted as inactive depicts inactive E. coli population)
Figure 10:
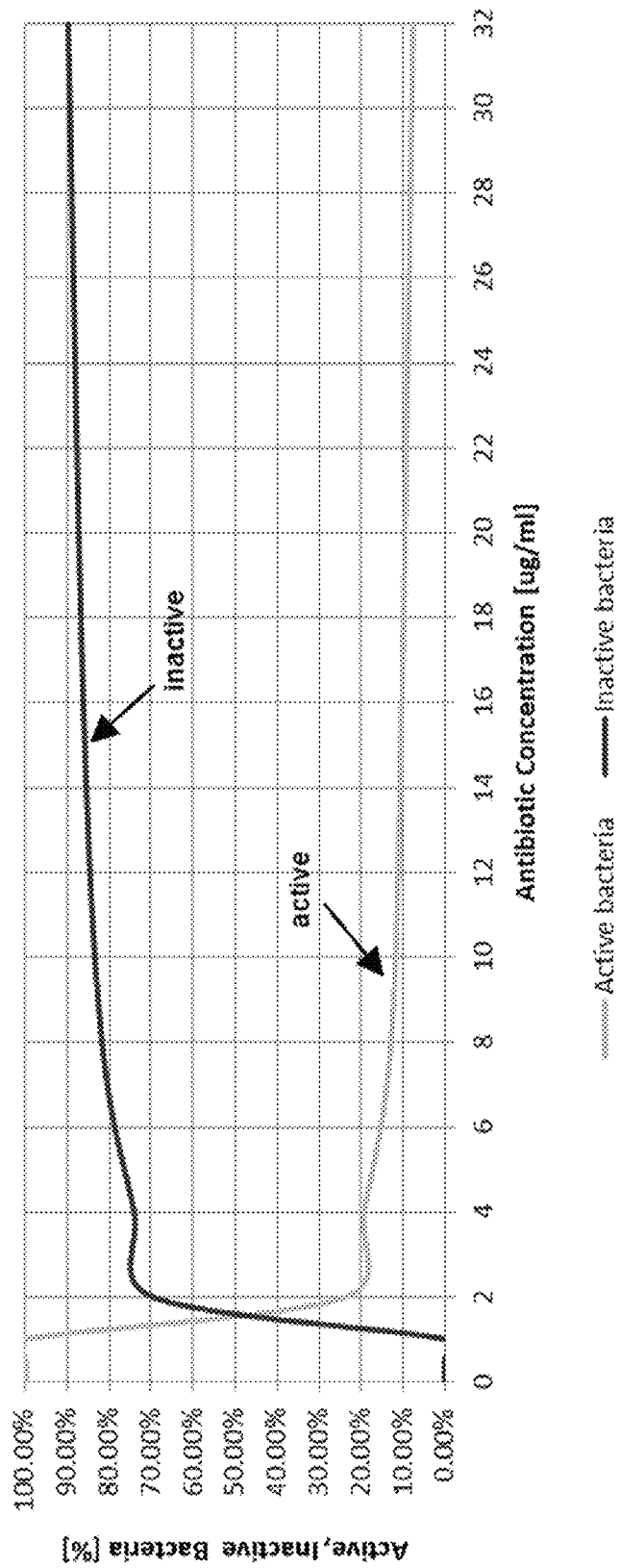
FIG. 10 shows active and inactive E. coli populations as a function of antibiotic concentration (lines respectively labeled active or inactive)
Figure 11:
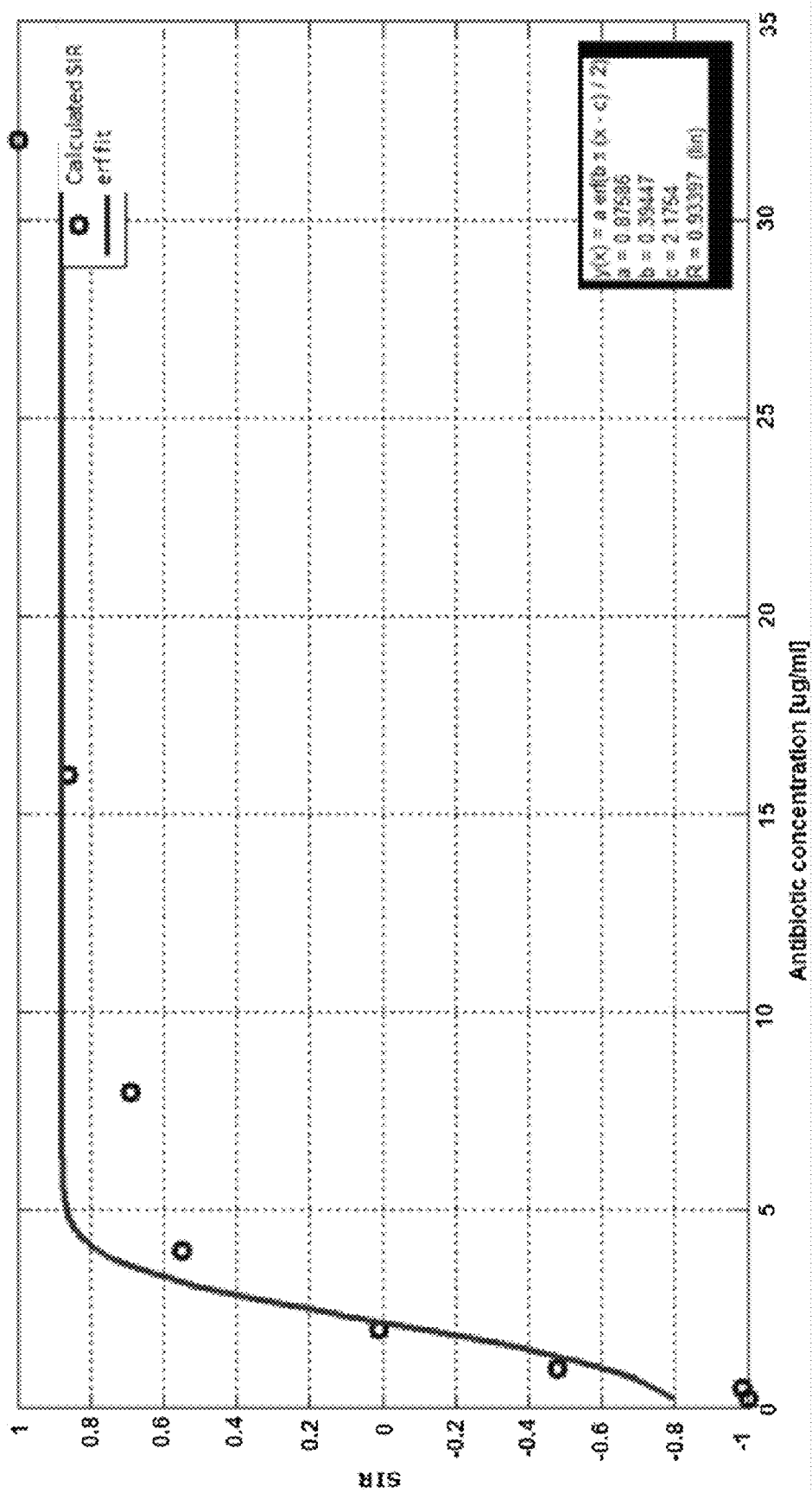
FIG. 11 shows spectral intensity ratio (SIR) as a function of antibiotic concentration for E. coli exposed to gentamicin treatment (circles note calculated SIR and solid line depicts approximated step function)

FIG. 9 shows fluorescence scatter plots (typical flow cytometric measurements) of E. coli treated with gentamicin. As can be seen from the figure, as long as the antibiotics concentration is below the MIC, the majority of the bacterium population is active (area noted as active in the scatter plot and FIG. 10). Once the antibiotic concentration reaches the MIC, the inactive bacterium population increases significantly (area noted as inactive in the scatter plot and FIG. 10). The increase in the inactive bacterial population increases the spectral intensity ratio (SIR) as can be seen in FIG. 11. The spectral intensity ratio (SIR) as a function of antibiotic concentration is approximated to a step function (solid line in FIG. 11) and the MIC is determined to be 2 μg/ml.

Figure 12:
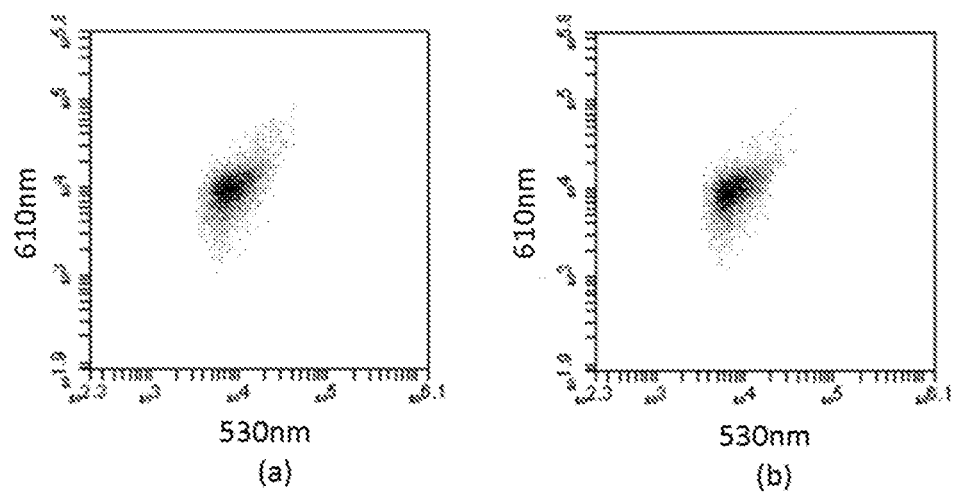
FIG. 12 shows a two wavelength fluorescence scatter plot of C. freundii resistant to gentamicin (panel (a) Control (not treated), and panel (b) 32 µg/ml)
Figure 13:
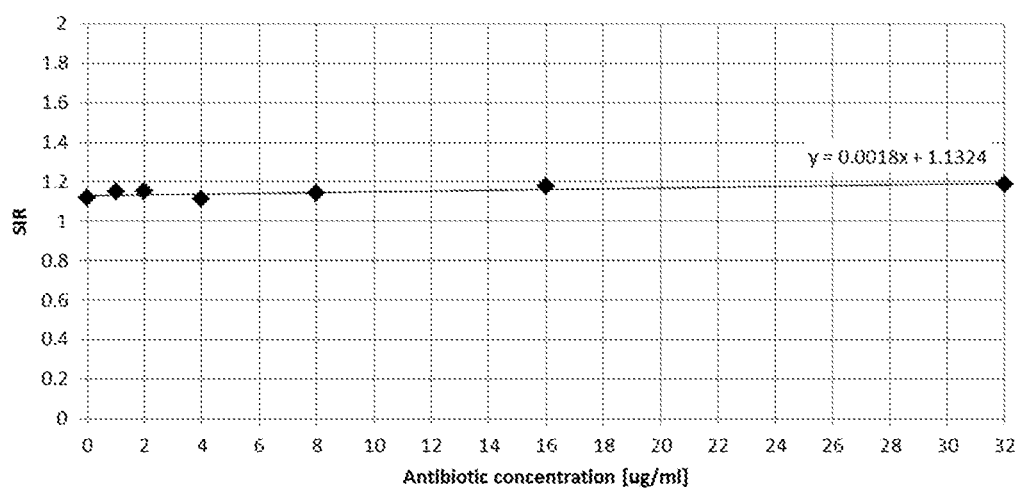
FIG. 13 shows spectral intensity ratio (SIR) as a function of antibiotic concentration of C. freundii resistant to gentamicin.

FIGS. 12 and 13 are examples of a resistant strain, C. freundii, which is resistant to gentamicin. As can be seen from FIG. 12, the flow cytometry fluorescence scatter plot remains practically the same even at high antibiotic concentrations. This is immediately reflected in the spectral intensity ratio (SIR) (FIG. 13), where the value remains almost constant.

The following tables summarize the performance of the method. The spectral intensity ratio (SIR) method has a 97.8% (88/90) essential agreement (the MIC result is within ±1 antibiotic dilution from the reference method), and 92.2% categorical agreement ("Class II Special Controls Guidance Document: Antimicrobial Susceptibility Test (AST) Systems," Aug. 28, 2009, FDA). The only errors were minor errors ("Class II Special Controls Guidance Document: Antimicrobial Susceptibility Test (AST) Systems," Aug. 28, 2009, FDA). Tables 3 and 4 present the results of the positive blood sample experiment using the macro dilution as the reference method. As can be seen from Table 3 the essential agreement is 98.4% and categorical agreement is 100%. There are no errors as defined by "Class II Special Controls Guidance Document: Antimicrobial Susceptibility Test (AST) Systems," Aug. 28, 2009, FDA.

Table 4 presents the method accuracy by showing how many samples were the same MIC value as the reference method, and how many deviated from the MIC value of the reference method and by how many dilutions. As can be seen from Table 2 the majority of the results are within +/−1 of the MIC value, which is an acceptable result by the FDA.

TABLE 3

Results analysis

| Antimicrobial agent | No. of Strains | Reference Method Susceptibilities | | | Essential Agreement | | Categorical Agreement | | Minor error | | Major error | | Very major error | |
|---|---|---|---|---|---|---|---|---|---|---|---|---|---|---|
| | | S | I | R | No. | % | No. | % | No. | % | No. | % | No. | % |
| Ampicillin | 30 | 16 | 5 | 9 | 30 | 100.0% | 27 | 90.0% | 3 | 10.0% | 0 | 0.0% | 0 | 0.0% |
| Gentamicin | 30 | 21 | 4 | 5 | 30 | 100.0% | 27 | 90.0% | 3 | 10.0% | 0 | 0.0% | 0 | 0.0% |
| Ciprofloxacin | 30 | 19 | 2 | 9 | 28 | 93.3% | 29 | 96.7% | 1 | 3.3% | 0 | 0.0% | 0 | 0.0% |
| Total percentage | | | | | | 97.8% | | 92.2% | | 7.8% | | 0.0% | | 0.0% |

TABLE 4

MIC Agreement

| Antimicrobial agent | Range [µg/ml] | Essential agreement [%] | Deviation from the MIC | | | | | | | | | | | |
|---|---|---|---|---|---|---|---|---|---|---|---|---|---|---|
| | | | <=-5 | -4 | -3 | -2 | -1 | 0 | 1 | 2 | 3 | 4 | >=5 | total |
| Ampicillin | 0.125-32 | 100.0% | 0.0% | 0.0% | 0.0% | 0.0% | 16.7% | 76.7% | 6.7% | 0.0% | 0.0% | 0.0% | 0.0% | 100.0% |
| Gentamicin | 0.125-32 | 100.0% | 0.0% | 0.0% | 0.0% | 0.0% | 23.3% | 66.7% | 10.0% | 0.0% | 0.0% | 0.0% | 0.0% | 100.0% |
| Ciprofloxacin | 0.0078-32 | 93.3% | 0.0% | 0.0% | 0.0% | 3.3% | 3.3% | 46.7% | 43.3% | 3.3% | 0.0% | 0.0% | 0.0% | 100.0% |

This study shows that antimicrobial susceptibility testing can be conducted using a single dye stain and flow cytometry measurement. By defining the spectral intensity ratio (SIR) parameter and plotting it as a function of the antibiotic concentration, it is possible to determine the MICs and whether it is susceptible, intermediate or resistant to a certain antibiotic. The spectral intensity ratio (SIR) method is done within 15 min following 2-4 hours of antibiotic treatment. Although the example included blood culture, it can likewise be used to determine other bacteria, such as found in urine or a clinical isolate.

An aspect of the present invention is that the specific bacteria does not have to be identified prior to the determination of the MIC. However, preclassification of the bacteria can be conducted using an analyzer, such as the Pocared P1000 which is described in U.S. Pat. Nos. 8,309,897, 8,804,114, 8,808,649, and 8,519,358 incorporated herein by reference. Also, the initial concentration of the blood or urine can occur via centrifugation described in the above-identified patents or through filtration such as described in U.S. Patent Application Publication Nos. 2011/0093207, 2012/0196271, 2014/0246389 and 2015/0152467, which are also herein incorporated by reference.

While the present invention has been described in terms of the above examples and detailed description, those of ordinary skill will understand that alterations may be made within the spirit of the invention. Thus, the present invention is capable of many variations in detailed implementation, which may be derived from the description contained herein by a person of ordinary skill in the art.

The invention claimed is:

1. A method for treating a patient suffering from a bacterial infection comprising the steps of:
   a. obtaining a minimum inhibitory concentration of one or more bacteria in a sample from the patient from a process comprising:
      i. preparing a plurality of bacterial suspensions of the one or more bacteria in a plurality of receptacles,
      ii. adding to the plurality of receptacles varying concentrations of an antimicrobial agent, thereby creating a plurality of suspensions comprising a combination of bacteria and antimicrobial agent,
      iii. incubating the plurality of suspensions comprising a combination of bacteria and antimicrobial agent of step ii. at a suitable temperature for a suitable period of time for bacterial culture, thereby creating a plurality of incubated suspensions comprising a combination of bacteria and antimicrobial agent,
      iv. adding to the suspensions of step iii. a single membrane-associated dye,
      v. illuminating in a cytometer the suspensions of step iv. with an incident light at one or more excitation wavelengths for the dye,
      vi. measuring in the cytometer intensity of emitted light at two emission wavelengths for the dye of each suspension, and
      vii. using data obtained from the cytometer of the measurement of the intensity of emitted light at two emission wavelengths of each suspension, determining a spectral intensity ratio (SIR) based upon step vi of each suspension, and determining the minimum inhibitory concentration of the antimicrobial agent for the one or more bacteria by determining the SIR as a function of the antimicrobial concentration in the form of:

$$y(x) = a \cdot \mathrm{erf}\left(\frac{b\pi(x-c)}{2}\right)$$

wherein a is a scaling parameter, b is the function slope, and c is the minimum inhibitory concentration value; and
   b. treating the patient with the antimicrobial agent at a concentration based upon at least the minimum inhibitory concentration defined by step vii.

2. The method of claim 1, wherein the single membrane-associated dye is a styryl dye or a cyanine dye.

3. The method of claim 1, wherein the single membrane-associated dye is N-(3-triethylammoniumpropyl)-4-(4-(dibutylamino)styryl)pyridinium dibromide.

4. The method of claim 1, wherein the excitation wavelength is between 360 nm and 570 nm.

5. The method of claim 1, wherein the two emission wavelengths are between 520 nm and 850 nm.

6. The method of claim 1, wherein the sample is a bodily fluid.

7. The method of claim 6, wherein the sample is blood or urine.

8. The method of claim 1, wherein the sample is a clinical isolate.

9. The method of claim 1, wherein the suitable incubation temperature is between 35° C. and 40° C.

10. The method of claim 1, wherein the suitable period of incubation time is between 30 minutes and 5 hours.

11. The method of claim 1, wherein by varying concentrations of an antimicrobial agent it is meant that the antimicrobial agent is prepared by serial dilutions.

12. The method of claim 1, wherein the sample is initially filtered to isolate the one or more bacteria in a concentrated form and is then diluted to a fixed concentration of bacteria.

13. The method of claim 12, wherein the dilution occurs with a liquid growth medium.

14. The method of claim 1, wherein the sample is initially concentrated via centrifugation and then diluted to a fixed concentration of bacteria.

15. The method of claim 1, wherein the varying concentrations are made with a liquid growth medium.

16. The method of claim 1, wherein the method includes removing a portion of each of the plurality of incubated suspensions comprising a combination of bacteria and antimicrobial agent and placing the portions in new receptacles after step iii.

17. The method of claim 1, wherein the illumination of step v. is at one wavelength.

18. The method of claim 1, wherein the SIR is determined using mean values of the intensity of emitted light at each of the two emission wavelengths.

19. A method of treating a patient suffering from a bacterial infection comprising the steps of:
   a. obtaining a minimum inhibitory concentration of one or more bacteria in a sample from the patient from a process comprising:
      i. preparing a plurality of bacterial suspensions of the one or more bacteria in a plurality of receptacles,
      ii. adding to the plurality of receptacles varying concentrations of an antimicrobial agent, thereby creating a plurality of suspensions comprising a combination of bacteria and antimicrobial agent,
      iii. incubating the plurality of suspensions comprising a combination of bacteria and antimicrobial agent of step ii. at a suitable temperature for a suitable period of time for bacterial culture, thereby creating a plurality of incubated suspensions comprising a combination of bacteria and antimicrobial agent,
      iv. adding to the suspensions of step iii. a single membrane-associated dye,
      v. illuminating in a cytometer the suspensions of step iv. with an incident light at one or more excitation wavelengths for the dye,
      vi. measuring in the cytometer intensity of emitted light at two emission wavelengths for the dye, and
      vii. using data obtained from the cytometer of the measurement of the intensity of emitted light at two emission wavelengths of each suspension, determining whether bacteria in the sample is susceptible, resistant or intermediate to antimicrobial treatment by determining a minimum inhibitory concentration of the antimicrobial agent for the one or more bacteria by determining a spectral intensity ratio (SIR) based upon step vi and as a function of the antimicrobial concentration in the form of:

$$y(x) = a * \text{erf}\left(\frac{b\pi(x-c)}{2}\right)$$

wherein a is a scaling parameter, b is the function slope, and c is the minimum inhibitory concentration value; and b. treating the patient with the antimicrobial agent at a concentration based upon at least the minimum inhibitory concentration defined by step vii.

20. The method of claim 19, wherein the illumination step v. is at one wavelength.

21. The method of claim 19, wherein the SIR is determined using mean values of the intensity of emitted light at each of the two emission wavelengths.

22. A method for treating a patient suffering from a bacterial infection comprising the step of:
   administering to the patient an antimicrobial agent at a concentration based upon a minimum inhibitory concentration of one or more bacteria in a sample from the patient, the minimum inhibitory concentration defined from a process comprising:
      i. preparing a plurality of bacterial suspensions of the one or more bacteria in a plurality of receptacles,
      ii. adding to the plurality of receptacles varying concentrations of the antimicrobial agent, thereby creating a plurality of suspensions comprising a combination of bacteria and antimicrobial agent,
      iii. incubating the plurality of suspensions comprising a combination of bacteria and antimicrobial agent of step ii. at a suitable temperature for a suitable period of time for bacterial culture, thereby creating a plurality of incubated suspensions comprising a combination of bacteria and antimicrobial agent,
      iv. adding to the suspensions of step iii. a single membrane-associated dye,
      v. illuminating in a cytometer the suspensions of step iv. with an incident light at one or more excitation wavelengths for the dye,
      vi. measuring in the cytometer intensity of emitted light at two emission wavelengths of the dye of each suspension, and
      vii. using data obtained from the cytometer of the measurement of the intensity of emitted light at two emission wavelengths of each suspension, determining the minimum inhibitory concentration of the antimicrobial agent for the one or more bacteria by determining a spectral intensity ratio (SIR) based upon step vi of each suspension, and determining the SIR as a function of the antimicrobial concentration, wherein the function is a step function that is in the form of:

$$y(x) = a * \text{erf}\left(\frac{b\pi(x-c)}{2}\right)$$

wherein a is a scaling parameter, b determines the step slope, and c is the minimum inhibitory concentration value.

* * * * *